(12) United States Patent
Park et al.

(10) Patent No.: US 8,753,881 B2
(45) Date of Patent: Jun. 17, 2014

(54) METHOD FOR INDUCING DIFFERENTIATION OF MESENCHYMAL STEM CELLS TO NERVE CELLS USING SOUND WAVES

(75) Inventors: Jung-Keug Park, Seoul (KR); Moon Young Yoon, Seoul (KR); Hyun Jin Cho, Seoul (KR); Young-Kwon Seo, Seoul (KR); Song Hee Jeon, Seoul (KR); Hee Hoon Yoon, Gyeonggi-do (KR)

(73) Assignee: Dongguk University Industry-Academic Cooperation Foundation, Seoul (KR)

( * ) Notice: Subject to any disclaimer, the term of this patent is extended or adjusted under 35 U.S.C. 154(b) by 0 days.

(21) Appl. No.: 13/702,982

(22) PCT Filed: Jun. 8, 2011

(86) PCT No.: PCT/KR2011/004191
§ 371 (c)(1),
(2), (4) Date: Feb. 12, 2013

(87) PCT Pub. No.: WO2012/053719
PCT Pub. Date: Apr. 26, 2012

(65) Prior Publication Data
US 2013/0202566 A1  Aug. 8, 2013

(30) Foreign Application Priority Data
Oct. 19, 2010 (KR) ........................ 10-2010-0101652

(51) Int. Cl.
*C12N 5/00* (2006.01)
*C12N 5/079* (2010.01)
*C12N 5/077* (2010.01)

(52) U.S. Cl.
USPC ........................................ 435/325; 435/377

(58) Field of Classification Search
None
See application file for complete search history.

(56) References Cited

U.S. PATENT DOCUMENTS

| 2005/0075679 | A1 | 4/2005 | Gliner et al. |
| 2006/0205993 | A1 | 9/2006 | Fischell et al. |
| 2007/0065941 | A1 | 3/2007 | Kondo et al. |
| 2010/0239544 | A1 | 9/2010 | Simon |

FOREIGN PATENT DOCUMENTS

| JP | 2008543388 | | 6/2006 |
| KR | 20050044849 | | 5/2005 |
| KR | 20080068351 | | 7/2008 |
| KR | 20090055691 | | 6/2009 |
| WO | WO 2005/045008 | * | 5/2005 |
| WO | WO 2009/142454 | * | 11/2009 |

OTHER PUBLICATIONS

Angle et al Ultrasonics 51: 281-288, published online Sep. 26, 2010.*
Oliveira et al (Curr Alzh Res 2: 79-95, 2005; abstract).*
Alexanian et al., "In Vitro and In Vivo Charactreization of Neurally Modified Mesenchymal Stem Cells Induced by Epigenetic Modifiers and Neural Stem Cell Environment", Stem Cells and Development, vol. 17:1123-1130 (2008).
Anghileri et al., "Neuronal Differentiation Potential of Human Adipos-Derived Mesenchymal Stem Cells" Stem Cells and Development, vol. 17:909-916 (2008).
Boucherie et al."Adult Stem Cell Therapoes for Neurological Disorders: Benefits Beyond Neuronal Replacement?", Journal of Neuroscience Research, vol. 87:1509-1521 (2009).
Croft et al., "Mesenchymal Stem Cells Expressing Neural Antigens Instruct a Neurogenic Cell Fate on Neural Stem Cells", Experimental Neurology, vol. 216:329-341 (2009).
Hofstetter et al., "Allodynia Limits the Usefulness of Intraspinal Neural Stem Cell Grafts; Directed Differentiation Improves Outcome", Nature Neuroscience, vol. 8(3):346-353 (Mar. 2005).
Kokai et al., "The Potential of Adipose-Derived Adult Stem Cells as a Source of Neuronal Progenitor Cells", American Society of Plastic Surgeons, vol. 116(5):1453-1460 (Nov. 23, 2004).
Kuh et al., "Functional Recovery Aftre Human Umbilical Cord Blood Cells Transplantation with Brain-Derived Neutrophic Factor into the Spinal Cord Injured Rat" Acta Neurochir, vol. 147:985-992 (2005).
Longhi et al., "Ex Vivo Gene Therapy Using Targeted Engraftment of NGF-Expressing Human NT2N Neurons Attenuates Cognitive Deficits Following Traumatic Brain Injury in Mice", Journal of Neurotrauma, vol. 21:1723-1736 (Nov. 12, 2004).
Matos et al. "Alternating Currect Electric Field Effects on Neural Stem Cell Viability and Differentiation", Biotechnology Progress, vol. 26:664-670 (2010).
Sun et al. "Effect of Pulsed Electromagetic Field on the Proiferation and Differentiation Potential of the Human Bone Marrow Mesenchymal Stem Cells" Bioelectromagnetics, vol. 30:251-260 (2009).
Xu et al., "Inhibition of Histone Deacetylase Activity in Reduced Oxygen Environment Enhances the Osteogenesis of Mouse Adipose-Derived Stromal Cells", Tissue Engineering: Part A, vol. 15(12):3697-3707 (Jul. 20, 2009).
International Search Report and Written Opinion from corresponding PCT Application No. PCT/KR2011/004191, 11 pages, dated Jan. 6, 2012.

* cited by examiner

*Primary Examiner* — Daniel E Kolker
*Assistant Examiner* — Aditi Dutt
(74) *Attorney, Agent, or Firm* — Dardi & Herbert, PLLC; Curtis B. Herbert (57) ABSTRACT

The present invention relates to a method for differentiation of mesenchymal stem cells. More specifically, the invention relates to a method for differentiating mesenchymal stem cells to neural cells by treating the mesenchymal stem cells with low-frequency sound waves. The differentiation method of the present invention can induce differentiation even with low-cost media rather than induced neural differentiation mediums which are expensive due to addition of growth factors, and the neural cells differentiated according to the present invention may be useful for treatment of neurological diseases.

6 Claims, 12 Drawing Sheets

METHOD FOR INDUCING DIFFERENTIATION OF MESENCHYMAL STEM CELLS TO NERVE CELLS USING SOUND WAVES

CROSS REFERENCE TO RELATED APPLICATIONS

This application is a national stage filing of PCT Application PCT/KR2011/004191 filed Jun. 8, 2011, which claims priority to Korean Patent Application No. 10-2010-0101652 filed Oct. 19, 2010, both of which applications are hereby incorporated by reference herein.

TECHNICAL FIELD

The present invention relates to a method for differentiation of mesenchymal stem cells. More specifically, the present invention relates to a method for differentiating mesenchymal stem cells into neural cells by applying a sound wave of a specific frequency to the mesenchymal stem cells.

BACKGROUND ART

Since neural cells have been used as a candidate material for treatment of cranial nerve diseases such as Alzheimer's disease, depression, Parkinson's disease, cerebral infarction, cerebral hemorrhage, spinal cord injury, etc., extensive research related to neural cells has recently been actively conducted, and a number of papers and patens have been disclosed. However, the neural cells or neural stem cells are difficult to obtain, and thus many studies related to differentiation of mesenchymal stem cells, which are relatively easy to obtain, into neural cells have been conducted. According to Lauren's review paper (*Plast. Reconstr. Surg.* 116:1453, 2005), among six reports on differentiation of fat-derived mesenchymal stem cells into neural cells in vitro by a chemical method, differentiated neural cells exhibiting functionally significant electrophysiological properties have been reported in one case. According to Arshak (*Stem Cells and Development*, 17: 1123-30, 2008), the differentiation of bone marrow-derived mesenchymal stem cells into neural cells was induced by chemical differentiation, and differentiated neuronal markers were investigated by immunohistochemistry, Western blot (B3T, GFAP, MAP-2, NeuN), ELISA (nerve growth factor (NGF), brain-derived neurotrophic factor (BDNF)), etc. to observe their properties, but the electrophysiological properties were not found. Research aimed at using mesenchymal stem cells in neurological treatment by mixed culture of neural cells or neural precursor cells has been conducted (Croft A P, *Exp. Neurol.*, 216(2): 329-41 (2009)), but it is practically impossible to obtain a sufficient amount of human neural cells or neural precursor cells used in the mixed culture. As another research direction, a study of inducing overexpression of neuronal genes using lentivirus to improve the differentiation has been conducted (Watson, D. J., *Journal of Neurotrauma*, 21:1723-36. (2004), Hofstetter, C., *Nature Neuroscience*, 8: 346-53. (2005)), but the safety of the virus has not been ensured, which makes it difficult to apply to cell therapy.

According to Kuh et al. (*Acta Neurochir* 147:985-992, 2005), at 8 weeks after transplantation of human umbilical cord blood cells into mice with spinal cord injuries, similar results were observed in Basso, Beattie and Bresnahan (BBB) scores compared with the control group with media alone, and at 5 weeks after transplantation of human umbilical cord blood cells mixed with brain-derived neurotrophic factor (BDNF), similar results were obtained, from which it can be seen that the simple transplantation of stem cells has limitations. According to Rooney et al. (*Tissue Engineering Part A*, Mar. 31, 2009), after transplantation of glial cell line-derived neurotrophic factor (GDNF) genes into bone marrow-derived mesenchymal stem cells isolated from fluorescent protein mice, it was observed that the stem cells into which the glial cell line-derived neurotrophic factor genes were introduced survived for 6 weeks. However, after transplantation of mesenchymal stem cells alone, the transplanted cells were not observed after 2 weeks, and thus it was reported that the transplantation of mesenchymal stem cells alone was insufficient for the treatment of spinal cord injuries.

One known neurological treatment technique using waves includes a system for applying a low-frequency of approximately 10 Hz to a patient's brain tissue, in which direct electrical stimulation is applied to electrodes implanted in or on the patient's brain to cause a magnetic field due to electrical currents (US20060205993). Zheng discloses a magnetic stimulation apparatus for central nervous system, in which the magnetic stimulation with a precise wave form, high frequency or a combination of a plurality of frequency components is used for improvement of brain function (JP2008-543388). Riken discloses a method for preparing neural cells by electric pulse treatment of embryonic stem cells (US20070065941). Gliner et al. disclose a method for preparing neural cells by electric pulse treatment of cells (US20050075679). However, the above techniques employ direct implantation of electrodes, which involve electrode implant surgery that causes pain to patients. In the case of embryonic stem cells, the possibility of tumor formation is raised, and there are limitations in their application to clinical trials.

Accordingly, an effective method that can differentiate mesenchymal stem cells, which are easy to obtain, into neural precursor cells, is urgently required.

SUMMARY

The present inventors, recognizing the above-described problems and needs, made extensive efforts to develop a method for inducing differentiation of mesenchymal stem cells, which are relatively easy to obtain, into neural cells so as to obtain neural cells or neural stem cells, which are difficult to obtain, and found that the treatment of stem cells with a sound wave of a specific frequency can induce differentiation of the stem cells, thus completing the present invention.

Accordingly, an object of the present invention is to provide a method for differentiation of mesenchymal stem cells into neural cells.

Another object of the present invention is to provide a composition for treatment of neurological diseases.

Technical Solution

To achieve the above objects, the present inventors provide a method for differentiation of mesenchymal stem cells into neural cells by applying a sound wave to the mesenchymal stem cells.

Moreover, the sound wave may preferably be applied at a frequency of 1 to 500 Hz and at an intensity of 0.1 to 5 V, and more preferably at a frequency of 30 to 300 Hz and at an intensity of 0.5 to 3 V.

The mesenchymal stem cells of the present invention may be derived from bone marrow, adipose, umbilical cord blood, or umbilical cord.

Furthermore, the present invention provides a composition for treatment of neurological diseases comprising the neural cells differentiated by the above-described method.

The neurological diseases may comprise Alzheimer's disease, depression, Parkinson's disease, cerebral infarction, cerebral hemorrhage, or spinal cord injury.

Advantageous Effects

The method and apparatus for differentiation of stem cells using sound waves according to the present invention can induce differentiation of adult stem cells into neural cells using low-frequency waves, which makes it possible to easily obtain neural cells or neural stem cells, which are difficult to obtain, can induce neuronal differentiation with neuronal differentiation induction media even under conditions of low-cost media, not with the neuronal differentiation induction media which are expensive due to the addition of growth factors, and thus can be effectively used for the treatment of cranial nerve diseases such as Alzheimer's disease, depression, Parkinson's disease, cerebral infarction, cerebral hemorrhage, spinal cord injury, etc.

DETAILED DESCRIPTION

The present invention relates to a method for differentiation of mesenchymal stem cells into neural cells by applying a sound wave to the mesenchymal stem cells.

The "sound wave" used in the present invention means that a change in pressure is partially caused in a medium (air), in which the vibration of an object is uniform, to vibrate the eardrum in the form of longitudinal waves. In the present invention, it is possible to induce differentiation of mesenchymal stem cells into neural cells by applying a vibration with a specific sound wave frequency of less than 20 kHz to the mesenchymal stem cells.

The "mesenchymal stem cells" used in the present specification may be derived from embryo, adult tissue, bone marrow, adipose, or umbilical cord.

Stem cells are undifferentiated cells that can divide over a long period of time, can self-renew, and can differentiate into various types of cells when certain conditions are given. Stem cells are divided into embryonic stem cells and adult stem cells according to their origin of tissue. The potential of adult stem cells is less than that of embryonic stem cells, but has no ethical issues, and thus many therapeutic agents have been studied on adult stem cells having no side effects.

Specifically, in the present invention, adult stem cells are used, which may be commercially available or isolated from living tissues.

The present invention relates to a method for differentiation of adult stem cells into neural cells by applying a sound wave of a specific frequency to the adult stem cells and has developed a technique for inducing neuronal differentiation of adult stem cells using sound waves in vitro.

Figure 1:
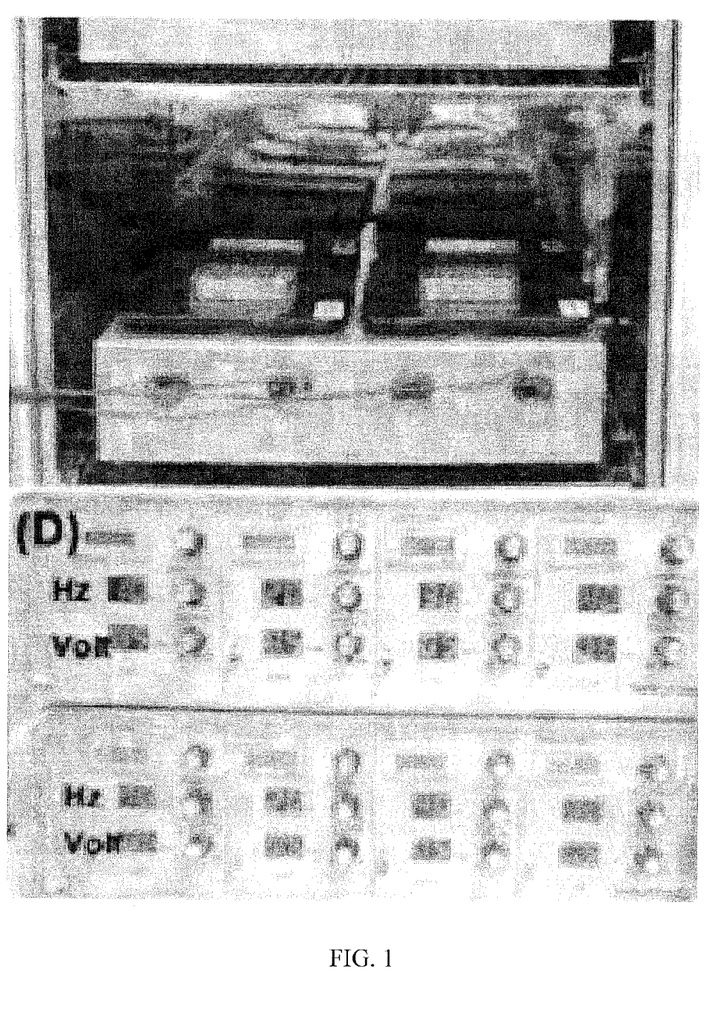
FIG. 1 shows the implementation of a sound wave generator for differentiation of adult stem cells in accordance with an embodiment of the present invention.
Figure 2:
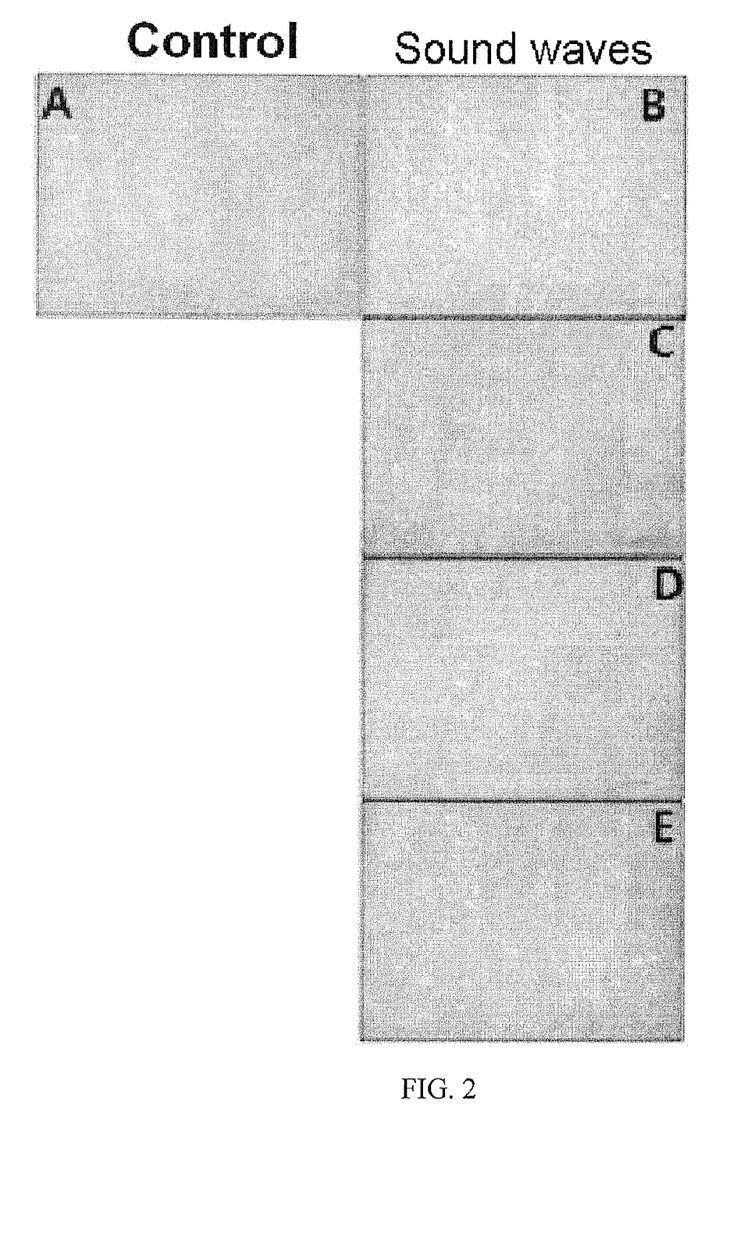
FIG. 2 shows the results of morphological changes of umbilical cord-derived mesenchymal stem cells after exposure to sound waves, observed using an optical microscope (A is a control, B was treated with 10 Hz, C was treated with 20 Hz, D was treated with 30 Hz, and E was treated with 40 Hz).
Figure 3:
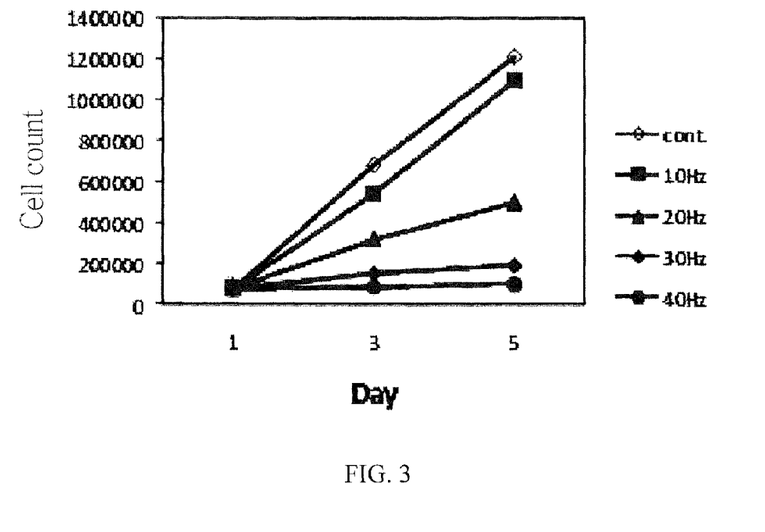
FIG. 3 shows the results of cell counts of umbilical cord-derived mesenchymal stem cells after exposure to sound waves (10 to 40 Hz).
Figure 4:
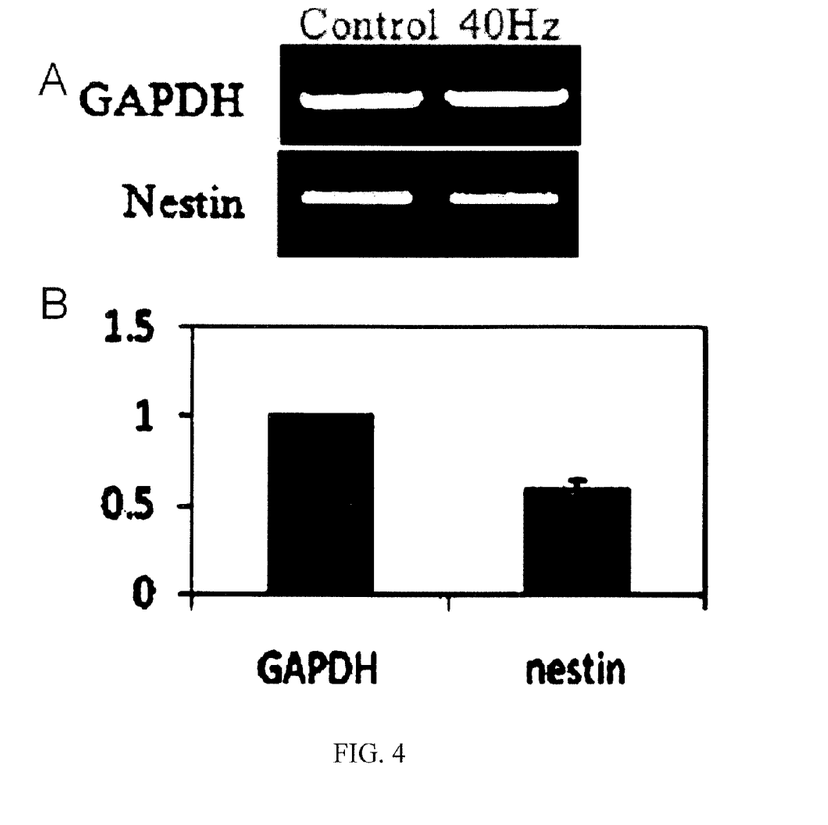
FIG. 4 shows the results of an experiment on the conditions for inducing neuronal differentiation of umbilical cord-derived mesenchymal stem cells, including the expression of Nestin, a mesenchymal stem cell marker, identified at mRNA level (A is RT-PCR and B is real-time PCR).
Figure 5:
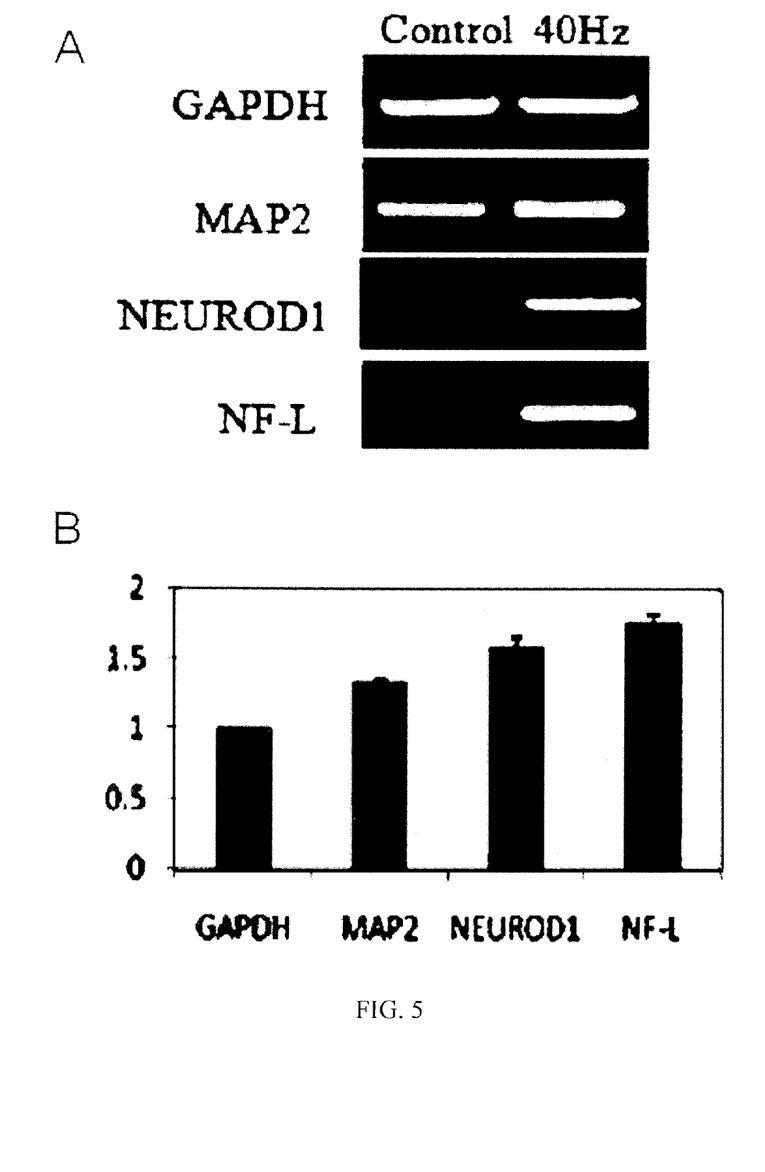
FIG. 5 shows the results of expression of neuronal mRNAs after inducing neuronal differentiation of umbilical cord-derived mesenchymal stem cells, including the expression of neuronal factors (MAP2, NeuroD1, and Neurofilament) after in vitro exposure to sound waves (A is RT-PCR and B is real-time PCR).
Figure 6:
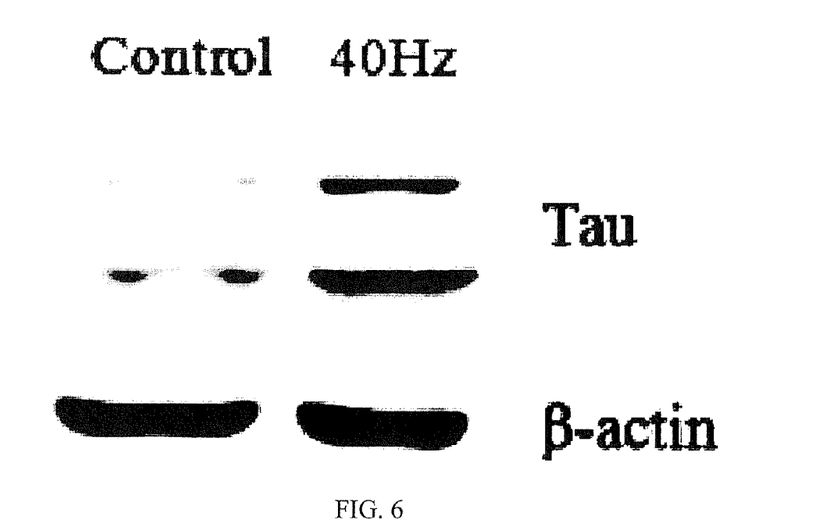
FIG. 6 shows the expression of neuronal protein (tau) after in vitro exposure to sound waves.

In an embodiment of the present invention (Example 1), after radiation of sound waves (10 to 40 Hz, 1.0 V) for 5 days using a sound wave generator shown in FIG. 1, mesenchymal stem cells were changed into neuron-like cells in the sound wave treatment groups (B to E), in particular at 30 to 40 Hz, compared to the non-treatment group (A) as shown in FIG. 2, and the proliferation of cells was not observed any longer, in particular at 30 to 40 Hz, from the measurement of cell counts as shown in FIG. 3. Moreover, the expression of Nestin was decreased only with the effects of sound waves in media without any growth factors (FIG. 4). After exposure to sound waves, the morphology of mesenchymal stem cells was changed, and the expression of neural stem cell markers such as NeuroD1 and Neurofilament was detected at mRNA level (FIG. 5). These effects of sound waves were also observed at protein level, and the expression of tau protein, a neuronal protein, was increased in the sample treated with sound waves for 5 days (FIG. 6).

Figure 9:
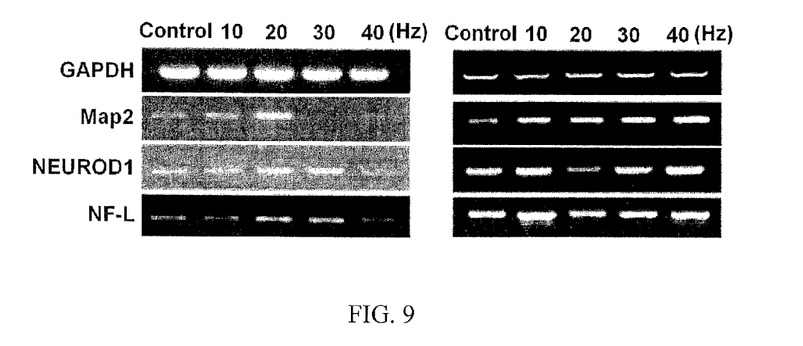
FIG. 9 shows the results of expression of neuronal mRNAs after inducing neuronal differentiation of bone marrow-derived and adipose-derived mesenchymal stem cells, including the expression of neuronal factors (MAP2, NeuroD1, and Neurofilament) after in vitro exposure to sound waves (A is bone marrow-derived mesenchymal stem cells and B is adipose-derived mesenchymal stem cells).

Moreover, in an embodiment of the present invention, after exposure of bone marrow-derived and adipose-derived mesenchymal stem cells to sound waves of 10 to 40 Hz at 1.0 V for 5 days, neuron-like cells were observed, and the proliferation of the cells was significantly decreased. Furthermore, analysis of the expression of neuronal markers at mRNA level revealed that the expression of MAP-2, NeuroD1, and NF-L was significantly increased, in particular at 30 or 40 Hz (FIG. 9).

Analysis of the differentiation into neural cells in a wider range of sound wave frequencies revealed that the differentiation into neural cells was promoted by the stimulation of sound waves in the range of 30 to 200 Hz at an intensity of 1 V.

Furthermore, analysis of the neuronal differentiation using sound waves at an intensity of 2.5 V revealed that the differentiation of umbilical cord-derived stem cells into neural cells was promoted at 30 to 300 Hz even at an intensity of 2.5 V as well as at 1 V.

Based on the above-described experimental results, the sound waves of the present invention may preferably be applied at a frequency of 1 to 500 Hz, more preferably 30 to 300 Hz, and most preferably 30 to 70 Hz. Moreover, the sound waves may preferably be applied at an intensity of 0.1 to 5 V, more preferably 0.5 to 3 V, and most preferably, 0.5 to 1.5 V.

The mesenchymal stem cells of the present invention can be cultured at 37° C. and 5% carbon dioxide atmosphere.

A sound wave generator for differentiation of mesenchymal stem cells according to the present invention may be configured as shown in FIG. 1. Moreover, for those not shown in FIG. 1, various techniques well known to those skilled in the art may be further included, which are within the sprit and scope of the present invention.

The method for differentiation into neural cells according to the present invention can induce neuronal differentiation even under growth medium conditions.

Furthermore, the present invention relates to a composition for treatment of neurological diseases comprising the neural cells differentiated by the above method.

The composition of the present invention uses neural cells differentiated from mesenchymal stem cells as a raw material and thus is non-toxic and safe.

The composition for treatment of neurological diseases may comprise pharmaceutical compositions well known to those skilled in the art in addition to the neural cells of the present invention and may be provided in the form of various formulations, which are within the sprit and scope of the present invention.

The composition may be formulated into a unit dosage form suitable for administration to a patient, and the composition comprises an effective dose that can develop alveoli by one or several administrations. The formulation suitable for this purpose may preferably be injections such as injectable ampoules for parenteral administration. The injectable ampoule may be mixed with an injection fluid before use, and the injection fluid may include saline solution, glucose, mannitol, Ringer's solution, etc.

The pharmaceutical preparation may further comprise one or more pharmaceutically acceptable inert carriers, for example, in the case of injections, preservatives, anesthetics, solubilizers, stabilizers, etc. and in the case of topical administration forms, bases, excipients, lubricants, preservatives, etc. in addition to the effective ingredient.

The composition or pharmaceutical preparation of the present invention prepared in the above manner may be administered in combination with other stem cells used for transplantation or other uses or in the form of a mixture with such stem cells by administration methods typically used in the art and may preferably be grafted or transplanted directly into a patient's lung disease area or transplanted or injected directly to the patient's respiratory tract, but not limited thereto. Moreover, the administration may include non-surgical administration using a catheter or surgical administration such as injection or transplantation after thoracic incision, and the non-surgical administration using a catheter is more preferable.

The neurological diseases of the present invention include all cranial nerve diseases such as Alzheimer's disease, depression, Parkinson's disease, cerebral infarction, cerebral hemorrhage, spinal cord injury, etc., and the neural cells or neural stem cells differentiated according to the present invention recover the functions of neural cells in neurological diseases and can function as a therapeutic agent for neurological diseases.

Next, the present invention will be described in more detail with reference to examples. However, the following examples are provided only for the purpose of illustrating the present invention, and the present invention is not limited by the following examples.

Reference Example 1

Isolation of Mesenchymal Stem Cells

Human umbilical cord expelled during childbirth was washed with phosphate buffer solution 3 times, and Wharton's jelly left after removal of smooth muscle and epithelium around blood vessels was cut into 3 mm×3 mm, placed in a culture vessel, and left in an incubator at 37° C. for about 4 hours such that the tissues were attached to the bottom of the vessel. When Dulbecco's Modification of Eagle's Medium (DMEM) containing 10% fetal bovine serum (FBS) was added to the culture vessel and cultured for 1 week, cells were isolated from the Wharton's jelly of the umbilical cord, and when more than 80% of cells were proliferated on the bottom of the culture vessel, the subculture was performed to use the subcultured cells as a cell source.

Example 1

Determination of Capacity to Induce Differentiation of Umbilical Cord-Derived Mesenchymal Stem Cells into Neural Cells Using Sound Waves (10 to 40 Hz) at Intensity of 1 Volt This example relates to a method for inducing differentiation of mesenchymal stem cells into neural cells using sound waves, and this method can induce neuronal differentiation even under growth medium conditions. Bone marrow-derived mesenchymal stem cells used in the experiment were obtained from Lonza, and adipose-derived mesenchymal stem cells were obtained from Invitrogen. NH media from Myltenyi were used as the growth media and cultured for 5 days. Primarily cultured umbilical cord-derived stem cells were subcultured 3 times in NH media and inoculated into a 100 mm culture dish at a density of $8 \times 10^4$ cells. All mesenchymal stem cells used in the experiment were cultured at 37° C. and 5% carbon dioxide atmosphere.

The umbilical cord-derived mesenchymal stem cells were exposed to sound waves at 10 to 40 Hz and 1.0 V for 5 days, and the results were observed. As can be seen from FIG. 2, the cells were changed into neuron-like cells, and the proliferation of cells were significantly decreased (FIG. 3). Analysis of the expression of neuronal markers at mRNA level revealed that the expression of MAP-2, NeuroD1, and NF-L was significantly increased, in particular at 30 to 40 Hz (FIG. 5), and the expression was very low at 10 to 20 Hz. Analysis of the expression of tau, a neuronal protein, at protein level revealed that the expression of tau protein was increased (FIG. 6). This means that the expression depends on the frequency, and it was determined that the stem cells were differentiated into neural cells at specific frequency and intensity.

Example 2

Determination of Capacity to Induce Differentiation of Bone Marrow-Derived and Adipose-Derived Mesenchymal Stem Cells into Neural Cells Using Sound Waves (10 to 40 Hz) at Intensity of 1 Volt NH media were used as the growth media in the same manner as the umbilical cord-derived mesenchymal stem cells and cultured for 5 days. Primarily cultured umbilical cord-derived stem cells were subcultured 3 times in NH media and inoculated into a 100 mm culture dish at a density of $8\times10^4$ cells. All mesenchymal stem cells used in the experiment were cultured at 37° C. and 5% carbon dioxide atmosphere.

Figure 7:
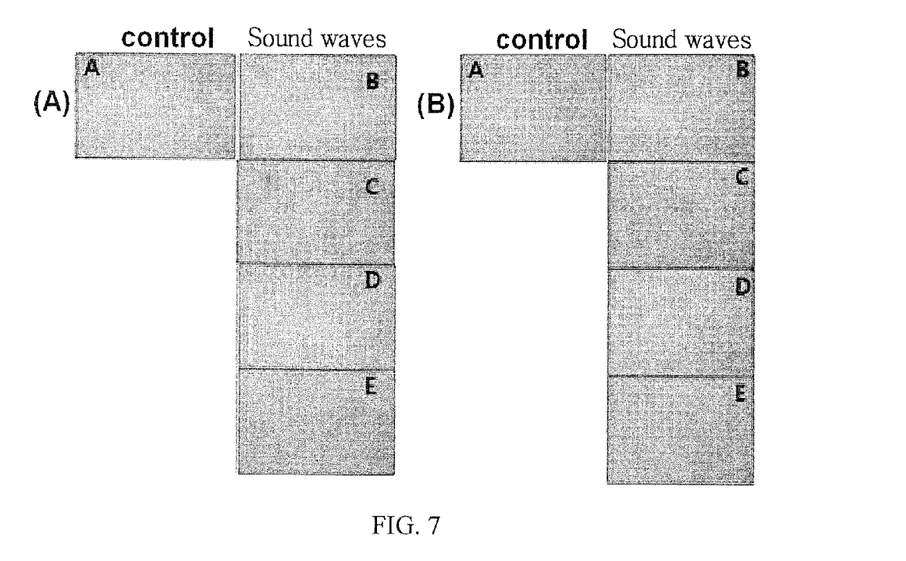
FIG. 7 shows the results of morphological changes of bone marrow-derived and fat-derived mesenchymal stem cells after exposure to sound waves, observed using an optical microscope (A is a control, B was treated with 10 Hz, C was treated with 20 Hz, D was treated with 30 Hz, and E was treated with 40 Hz).
Figure 8:
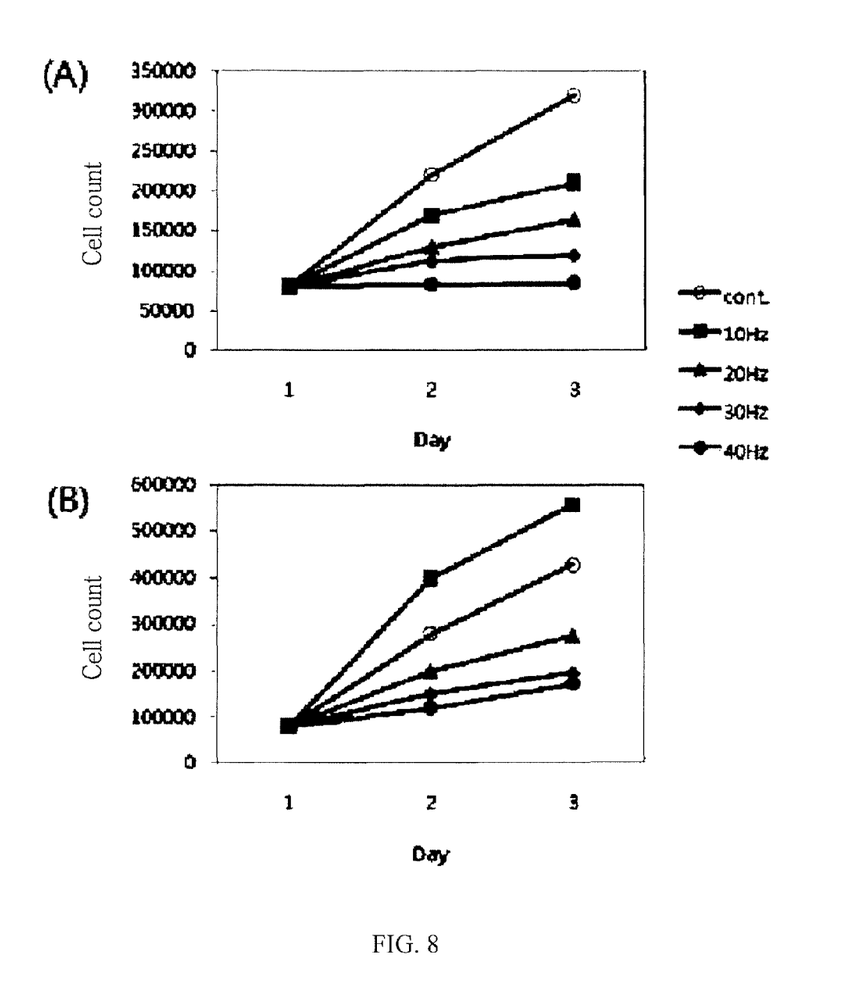
FIG. 8 shows the results of cell counts of bone marrow-derived and adipose-derived mesenchymal stem cells after exposure to sound waves (10 to 40 Hz).

The bone marrow-derived and adipose-derived mesenchymal stem cells were exposed to sound waves at 10 to 40 Hz and 1.0 V for 5 days, and the results were observed. As can be seen from FIG. 7, the cells were changed into neuron-like cells, and the proliferation of cells were significantly decreased (FIG. 8). Analysis of the expression of neuronal markers at mRNA level revealed that the expression of MAP-2, NeuroD1, and NF-L was significantly increased, in particular at 30 to 40 Hz (FIG. 9), and the expression was very low at 10 to 20 Hz. This means that the expression depends on the frequency, and it was determined that the stem cells were differentiated into neural cells at specific frequency and intensity.

Example 3

Determination of Induction of Neuronal Differentiation of Umbilical Cord-Derived Stem Cells Using Sound Waves (30 to 500 Hz) at Intensity of 1 Volt Primarily cultured umbilical cord-derived stem cells were subcultured 5 times in NH media and inoculated into a 100 mm culture dish at a density of $1\times10^5$ cells. In the stationary culture group, the simulation of sound waves was not applied to the cells, and the simulation of 30, 100, 200, 300, and 500 Hz sound waves (at an intensity of 1 V) was applied to the rest, respectively, and cultured in NH media for 3 days at 37° C. and 5% carbon dioxide atmosphere.

Figure 10:
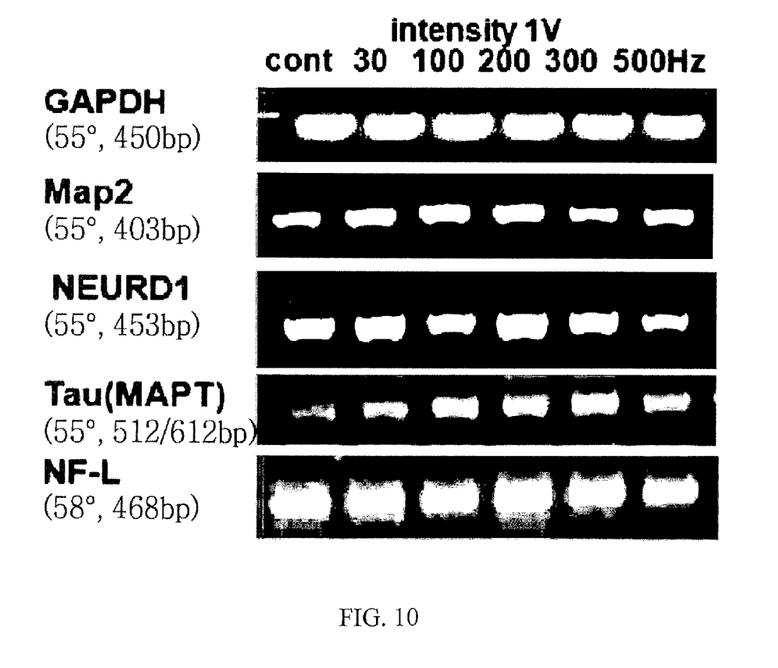
FIG. 10 shows the results of expression of neuronal markers of umbilical cord-derived mesenchymal stem cells after stimulation of 30 to 500 Hz sound waves at an intensity of 1 volt (V), obtained by mRNA analysis.
Figure 11:
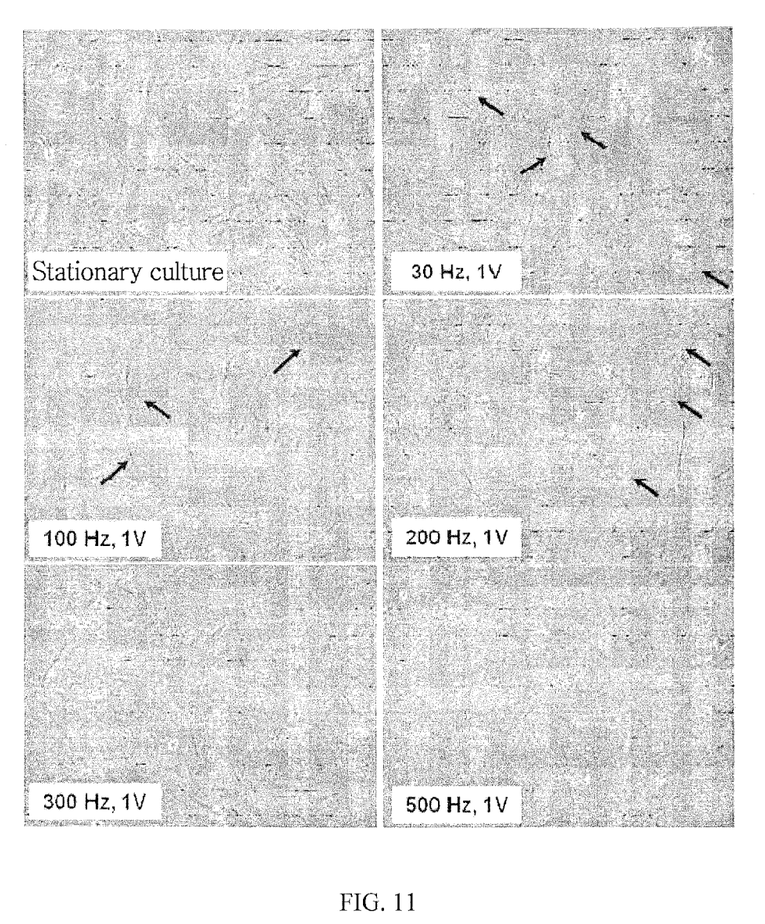
FIG. 11 shows the results of morphological changes of umbilical cord-derived mesenchymal stem cells after stimulation of 30 to 500 Hz sound waves at an intensity of 1 volt (V).

Analysis of the expression of neuronal markers at mRNA level revealed that the expression of MAP-2, NeuroD1, and tau was significantly increased, in particular at 30 to 200 Hz, and the expression of NF-L was significantly increased, in particular at 200 Hz, compared to the stationary culture group (FIG. 10). At this time, the morphological changes of cells were observed using an optical microscope and, as a result, neurites (shown by arrows) were formed at 30 to 200 Hz and changed into neuron-like cells, compared to the stationary culture group (FIG. 11).

That is, it could be seen that the differentiation of umbilical cord-derived stem cells into neural cells was promoted by the stimulation of sound waves of 30 to 200 Hz at an intensity of 1 V.

Example 4

Determination of Induction of Neuronal Differentiation of Umbilical Cord-Derived Stem Cells Using Sound Waves (30 to 500 Hz) at Intensity of 2.5 Volt Primarily cultured umbilical cord-derived stem cells were subcultured 6 times in NH media and inoculated into a 100 mm culture dish at a density of $1\times10^5$ cells. In the stationary culture group, the simulation of sound waves was not applied to the cells, and the simulation of 30, 100, 200, 300, and 500 Hz sound waves (at an intensity of 2.5 V) was applied to the rest, respectively, and cultured in NH media for 3 days at 37° C. and 5% carbon dioxide atmosphere.

Figure 12:
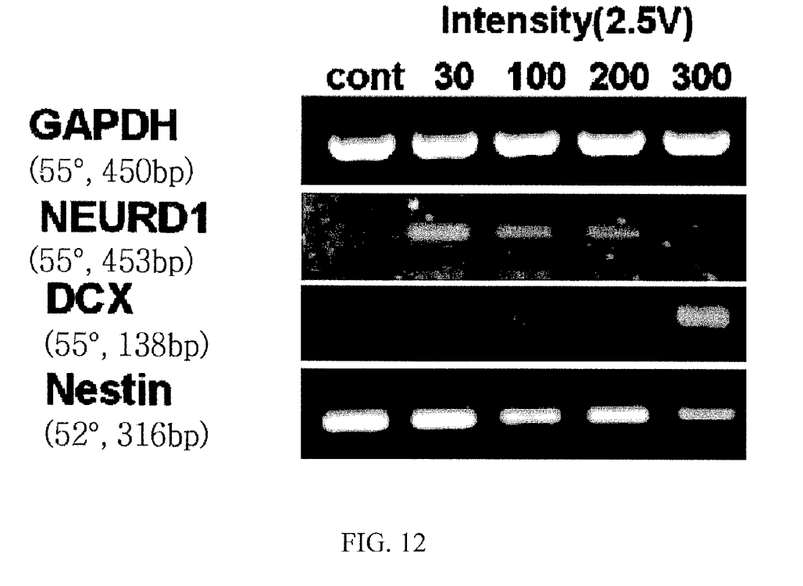
FIG. 12 shows the results of expression of neuronal markers of umbilical cord-derived mesenchymal stem cells after stimulation of 30 to 300 Hz sound waves at an intensity of 2.5 volt (V), obtained by mRNA analysis.
Figure 13:
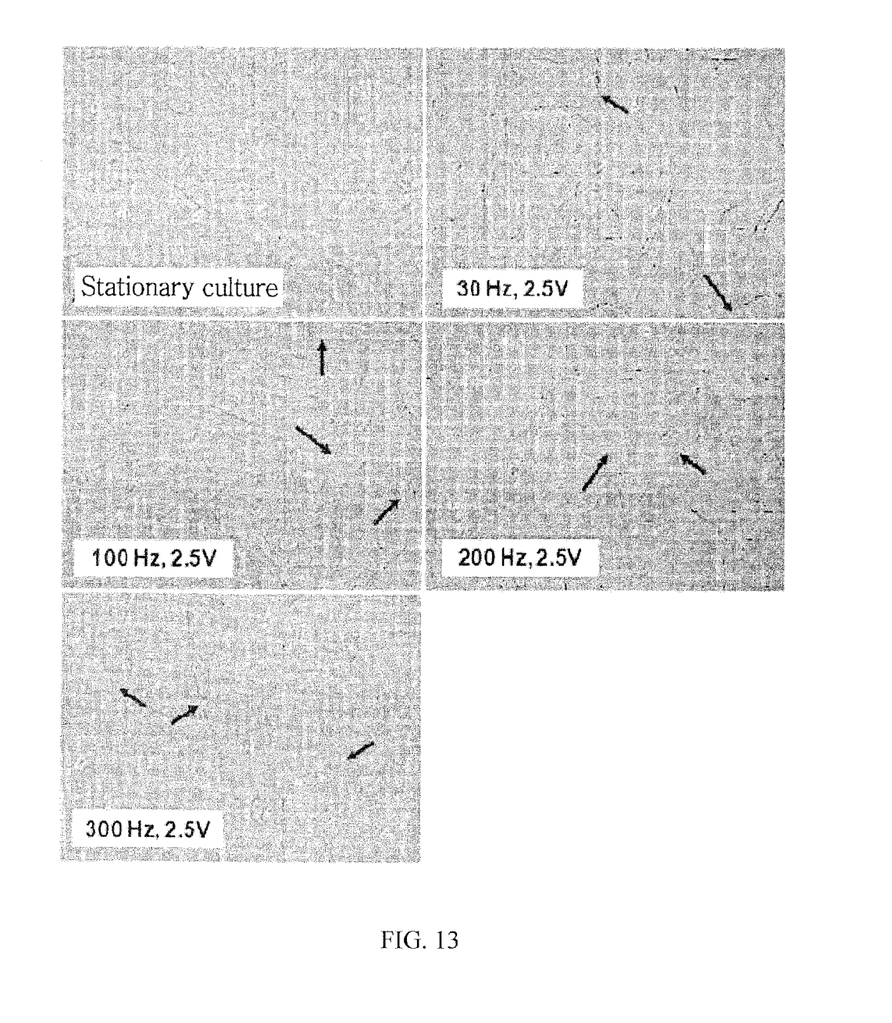
FIG. 13 shows the results of morphological changes of umbilical cord-derived mesenchymal stem cells after stimulation of 30 to 300 Hz sound waves at an intensity of 2.5 volt (V).

Analysis of the expression of neuronal markers at mRNA level revealed that the expression of NeuroD1 was significantly increased, in particular at 30 to 200 Hz, and the expression of DCX was significantly increased at 100 Hz and 300 Hz, compared to the stationary culture group. In particular, it could be found that as the expression of Nestin was decreased in all sound wave stimulation groups, the differentiation into neural cells proceeded (FIG. 12). At this time, the morphological changes of cells were observed using an optical microscope and, as a result, neurites (shown by arrows) were formed at 30 to 300 Hz and changed into neuron-like cells, compared to the stationary culture group (FIG. 13).

That is, it could be seen that the differentiation of umbilical cord-derived stem cells into neural cells was promoted even at an intensity of 2.5 V as well as at 1 V.

Example 5

Determination of Induction of Neuronal Differentiation of Bone Marrow-Derived Stem Cells Using Sound Waves (30 to 500 Hz) at Intensity of 1 Volt Primarily cultured bone marrow-derived stem cells were subcultured 6 times in low glucose DMEM/10% FBS media (Gibco) and inoculated into a 100 mm culture dish at a density of $1\times10^5$ cells. In the stationary culture group, the simulation of sound waves was not applied to the cells, and the simulation of 30, 100, 200, 300, and 500 Hz sound waves (at an intensity of 1 V) was applied to the rest, respectively, and cultured in low glucose DMEM/10% FBS media for 3 days at 37° C. and 5% carbon dioxide atmosphere.

Figure 14:
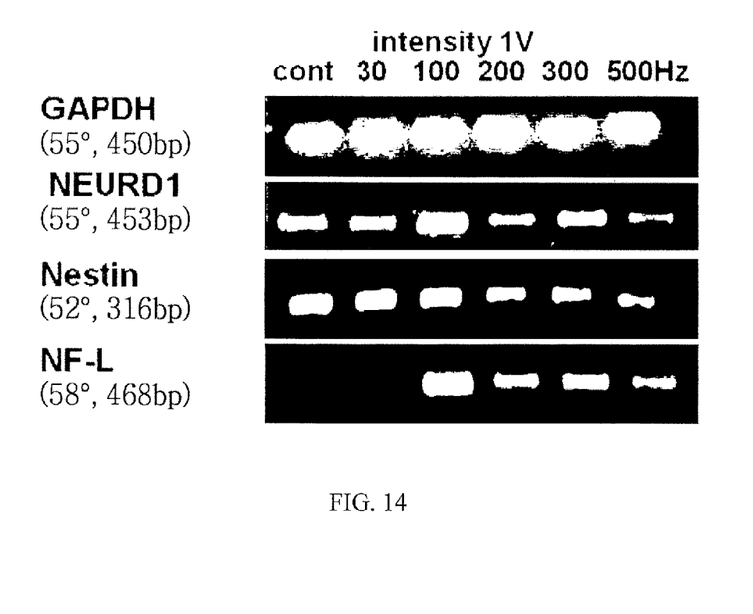
FIG. 14 shows the results of expression of neuronal markers of bone marrow-derived mesenchymal stem cells after stimulation of 30 to 500 Hz sound waves at an intensity of 1 volt (V), obtained by mRNA analysis.

Analysis of the expression of neuronal markers at mRNA level revealed that the expression of NeuroD1 and NF-L and was significantly increased, in particular at 100 Hz, compared to the stationary culture group. It could be found that as the expression of Nestin was decreased compared to the stationary culture group, the differentiation into neural cells proceeded (FIG. 14).

That is, it could be seen that the differentiation of bone marrow-derived stem cells into neural cells was promoted even at 100 Hz and an intensity of 1 V.

The method and apparatus for differentiation of stem cells using sound waves according to the present invention can induce differentiation of adult stem cells into neural cells using low-frequency waves, which makes it possible to easily obtain neural cells or neural stem cells, which are difficult to obtain, can induce neuronal differentiation even under conditions of low-cost media, not with neuronal differentiation induction media which are expensive due to the addition of growth factors, and thus can be effectively used for the treatment of cranial nerve diseases such as Alzheimer's disease, depression, Parkinson's disease, cerebral infarction, cerebral hemorrhage, spinal cord injury, etc.

The invention claimed is:

1. A method for differentiation of mesenchymal stem cells into neural cells comprising applying a sound wave having a frequency range of 30 to 300 Hz to the mesenchymal stem cells in a protocol sufficient to induce expression of neuronal markers.

2. The method of claim 1, wherein the sound wave is applied at an intensity of 0.1 to 5 V.

3. The method of claim 1, wherein the sound wave is applied at an intensity of 0.5 to 3 V.

4. The method of claim 1, wherein the mesenchymal stein cells are derived from bone marrow, fat, umbilical cord blood, or umbilical cord.

5. A method for differentiation of mesenchymal stem cells into neural cells comprising applying a sound wave having a frequency range of 30 to 300 Hz at an intensity of 0.1 to 5 V to the mesenchymal stem cells.

6. The method of claim 5, wherein the mesenchymal stem cells are derived from bone marrow, fat, umbilical cord blood, or umbilical cord.

* * * * *